United States Patent [19]

Mathias et al.

[11] 4,359,429
[45] Nov. 16, 1982

[54] MERCAPTOACETONITRILE SYNTHESIS

[75] Inventors: Eckart Mathias, Catonsville, Md.; Michael A. Shimanski, Smyrna, Ga.

[73] Assignee: W. R. Grace & Co., New York, N.Y.

[21] Appl. No.: 297,377

[22] Filed: Aug. 28, 1981

Related U.S. Application Data

[63] Continuation-in-part of Ser. No. 227,580, Jan. 23, 1981, abandoned, which is a continuation-in-part of Ser. No. 178,665, Aug. 18, 1980, abandoned.

[51] Int. Cl.$^3$ .................. C07C 120/00; C07C 121/16
[52] U.S. Cl. .......................... 260/465.1; 260/465.8 R
[58] Field of Search ...................................... 260/465.1

[56] References Cited

U.S. PATENT DOCUMENTS

| | | | |
|---|---|---|---|
| 2,404,425 | 7/1946 | Beanblossom et al. | 568/70 |
| 2,413,917 | 1/1947 | Harman | 260/465.1 X |
| 2,630,452 | 3/1953 | Crouch et al. | 260/465.1 |
| 2,762,836 | 9/1956 | Selcer | 260/465.8 R |
| 2,816,145 | 12/1957 | Chen-Hu Ch'in et al. | 568/70 |
| 3,211,777 | 10/1965 | Bikales | 260/465.1 |
| 3,280,164 | 10/1966 | Louthan | 260/465.1 |
| 3,502,708 | 3/1970 | Thoma et al. | 260/465.1 |
| 3,839,399 | 10/1974 | Starks et al. | 260/465.1 X |
| 3,992,432 | 11/1976 | Napier et al. | 260/465.1 X |

OTHER PUBLICATIONS

Reid, Organic Chemistry of Bivalent Sulfur, vol. I, (1958), pp. 25-28.

*Primary Examiner*—Joseph Paul Brust
*Attorney, Agent, or Firm*—Richard P. Plunkett; William W. McDowell, Jr.

[57] ABSTRACT

A method of synthesizing mercaptoacetonitrile which comprises reacting chloroacetonitrile with aqueous sodium hydrosulfide.

6 Claims, No Drawings

MERCAPTOACETONITRILE SYNTHESIS

This application is a continuation-in-part of our copending application having Ser. No. 227,580, filed Jan. 23, 1981, now abandoned, which is a continuation-in-part of our copending application having Ser. No. 178,665, filed Aug. 18, 1980, now abandoned.

PRIOR ART DESCRIPTION

Organic sulfur compounds including thionitriles are of considerable importance in the fields of the petroleum, plastics, synthetic rubbers and pharmaceutical industry.

Various processes have been disclosed in the prior art for the preparation of mercapto-substituted nitriles, but many of these have proven unsatisfactory for one reason or the other. The simple addition of hydrogen sulfide to unsaturated nitriles produces small yields of mercapto-substituted nitriles and a relatively larger quantity of the corresponding thioether (sulfide). If mild reaction conditions are used for the thiolation reaction, very long reaction times are required to produce even low yields of the mercapto-substituted nitrile.Examples of art teaching mercapto-substituted nitrile preparation via reaction of the nitrile with hydrogen sulfide can be found in U.S. Pat. No. 3,280,164 where the mercaptonitrile is prepared in the presence of a catalytic amount of sulfur and in U.S. Pat. No. 3,502,708, where mercaptopropionitrile is obtained via reaction of acrylonitrile with liquid hydrogen sulfide in the presence of an organic nitrogen base. Examples of teachings relating to mercaptonitrile preparation via reaction between alkyl mercaptans and unsaturated nitriles can be found in U.S. Pat. No. 2,413,917 and other means for preparing mercaptonitriles (e.g., β-mercapto-proprionitrile) include conversion of thiol acetic acid to the corresponding thiol acetate via reaction with an unsaturated nitrile (acrylonitrile) with subsequent hydrolysis of said thiol acetate to said mercaptonitrile, such art being documented by U.S. Pat. Nos. 2,630,452 and 3,211,777.

Other types of nitriles, e.g. thiodinitriles of the formula:

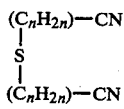

have been prepared by the reaction of β-chloro-propionitrile with sodium hydrosulfide and such teaching can be found in U.S. Pat. No. 2,762,836.

The foregoing and other methods of synthesizing mercaptonitriles often involve the need to use high pressure equipment and sometimes result in relatively poor yield products.

Reid, Orgnic Chemistry of Bivalent Sulfur, Volume 1, pp. 25-28 (1958), teaches the synthesis of mercaptans from alkyl halides and metal sulfhydrates using alcohol as a solvent. The alkyl halide is added dropwise to the metal sulfhydrate.

U.S. Pat. No. 2,816,145 teaches a process for forming methyl mercaptans using as raw materials methylchloride, hydrogen sulfide and a metal hydrosulfide in the presence of water as the sole solvent and temperatures between 20-70° C. Contacting of the reactants is carried out by continuous bubbling gaseous methyl chloride and hydrogen sulfide through a stationary batch of metal hydrosulfide solution.

U.S. Pat. No. 2,404,425 teaches the production of alkyl mercaptans by reacting the corresponding alkyl chloride with sodium hydrosulfide at temperatures in the range 70–100° C.

It is to be noted in the three latter prior art references that the reaction is carried out by either dropwise or gaseous continuous addition of one reactant to another, at temperatures above 0° C. Additionally, in these systems the product is an alky mercaptan and not a nitrile alkyl mercaptan.

The need has thus arisen for devising simple methods for synthesizing mercaptonitriles under mild conditions showing relatively good yields. Particularly, the need has arisen to devise methods to synthesize mercaptoacetonitrile which is less stable than β-mercapto-propionitrile and hence not as readily synthesizable.

BRIEF DESCRIPTION OF THE INVENTION

The present invention relates to a simplified, low pressure, low temperature method of producing good yields of mercaptoacetonitrile by means of the reaction of chloroacetonitrile (ClAN) with 10 to 50% aqueous sodium hydrosulfide (NaSH). High purity MAN can be obtained by vacuum distillation of the crude product. The reaction is preferably carried out using stoichiometric amounts of the ClAN and NaSH reactants. However, substantially stoichiometric amounts, i.e., up to a 2% molar excess of either reactant, is also operable to obtain high yields of MAN under the conditions herein.

DETAILED DESCRIPTION OF THE INVENTION

Mercaptoacetonitrile, hereinafter referred to as MAN for briefness, can be used in the synthesis of thioglycolic acid.

It has now been discovered that it is possible to synthesize MAN by means of a simple, atmospheric-pressure, low temperature process described as follows.

A substantially stoichometric amount of chloroacetonitrile is reacted with 10 to 50 weight %, preferably 30 to 40 weight % aqueous sodium hydrosulfide, under an inert atmosphere, such as nitrogen, helium and the like, to prevent the oxidation of MAN. The weight % of water in the aqueous sodium hydrosulfide includes any water of hydration contained in commercially available sodium hydrosulfide. The reaction can also be run under a reducing atmosphere including, but not limited to, hydrogen sulfide, hydrogen, carbon monoxide and the like and mixtures of such reducing atmospheres. The reaction is run at substantially atmosheric pressure. That is, since an inert or reducing blanket is employed, the pressure in the reaction chamber ranges from about atmospheric up to about 30 mm Hg above atmospheric pressure. The reaction exotherms when the pH of the reaction mixture is in the range of 8.0–9.5 under the conditions herein.

It is critical in the instant process in order to obtain high yields that the chloroacetonitrile be added in mass, i.e., all at once to the aqueous sodium hydrosulfide. Incremental or dropwise addition results in little or no yield as will be shown in an example hereinafter. It is also critical in order to obtain high yields that the reaction be run at low temperatures, i.e., below 0° C., preferably below −10° C. Best temperatures are those which are low enough to effect a good yield reaction and yet not so low as to freeze up the reaction mixture or starting reagents. An appropriate choice of a liquid medium which will prevent the lumping of frozen solids such as the NaSH solution will allow low temperatures to be used without completely freezing up the reaction system. Such liquid media include, but are not limited to, methylene chloride, methyl chloride, ethyl chloride, isopropanol, ethylene glycol, glycerin and the like. If the reaction is carried out in the presence of a liquid medium, salts such as tricaprylylmethyl ammonium chloride, triethyl benzyl ammonium chloride, hexadecyltributyl phosphonium bromide, tetrabutyl ammonium bisulfate and the like improve the product yield. These salts are added in amounts ranging from 0.05 to 5% by weight of the chloroacetonitrile. After the final workup (solvent extraction and low pressure distillation) the analysis of the product (MAN) indicates a purity of 100%.

The yield of MAN can be increased considerably by subjecting the reaction product mixture to a reducing agent. These reducing agents are well known to those skilled in the art and include, but are not limited to, triphenylphosphine, hydrogen sulfide, stannous chloride and the like.

The following exmaples further illustrate the practice of the present invention, but is should be understood that conditions recited therein are not to be construed so as to limit unduly this invention. All parts and percentages are by weight unless otherwise noted.

EXAMPLE 1

To 3-neck, 500 ml, round bottomed flask eqipped with stirrer, condenser, thermometer and pH probe was added under $N_2$ blanket, 15.32 g (0.273 moles) NaSH (NaSH hydrate of 25.6% water content) and 20 ml of distilled water. After cooling this mixture to $-20°$ C., 20.64 g (0.273 moles) of ClAN was added at once. The total mixture was then kept at $-20°$ C. The initial pH of this reaction mixture was above 12. During the next 15 minutes the pH decreased to 8.4 at which point the mixture exothermed. The temperature increased rapidly to 33° C. After the exotherm a white solid came out of solution (identified as NaCl). Thirty minutes after the exotherm occurred (keeping the reaction mixture at or near 0° C.) the reaction mixture was worked up as follows:

While still in the reaction flask, enough 25% aqueous $H_2SO_4$ was added to the reaction mixture to take the pH below 2.0 (took 5 ml).

Vacuum was then applied to the flask to remove any $H_2S$ generated during the acidification step above.

The reaction mixture was then placed in a one-half liter separatory funnel and enough water was added to dissolve the NaCl, plus another 5 ml of 25% aqueous $H_2SO_4$ was added.

The MAN was extracted with three 25 ml portions of methylene chloride.

The methylene chloride was then stripped by vacuum distillation.

The resultant product was determined to be 50.5% MAN by iodine titration (mixture SH=6.9 meq/g, theory for 100% MAN=13.67). The MAN was distilled from this mixture at 34° C. at 2 torr and 39° C. at 5 torr. The analysis of the distilled MAN gave an SH of 14.0 meq/g (102.4% of theory). The identity of MAN was confirmed by infrared spectroscopy (IR).

Synthesis with similar or identical procedures led to MAN, the identity of which was established by IR, proton NMR and C-13 NMR.

EXAMPLE 2

To a 3-neck, 500 ml, round bottomed flask, equipped with stirrer, condenser, thermometer and pH probe, was added under nitrogen blanket 38.3 g (0.683 moles) NaSH (NaSH hydrate of 30.6% water content) and 55 ml of distilled water. After cooling this mixture to $-17°$ C., 51.54 g (0.683 moles) of ClAN was added at once. The initial pH of this reaction mixture was above 12. During the next 37 minutes, the pH decreased to 8.4 while the temperature was maintained between $-15°$ and $-22°$ C. While the temperature increased gradually to $-15°$ C., a white solid came out of solution (identified as NaCl). The reaction mixture was kept another 30-35 minutes between $-15°$ and 0° C., after which it was worked up as described in Example 1.

The resultant product mixture was determined to be 53.4% MAN by iodine titration (mixture SH=7.3 meq/g, theory for 100% MAN=13.67). .p A portion of this reaction mixture was then subjected to a reduction step as follows To a 500 ml Erlenmeyer flask, equipped with magnetic stirrer, was added under nitrogen 5.0 g of the reaction mixture, 70.0 g of methanol and 1.1 g of N/10 HCl solution. The SH content of this mixture was then determined to be 0.48 meq/g by iodine titration. To this reaction mixture was then added 4.5 g of triphenylphosphine and the total mixture was then stirred for one hour at room temperature. At the end of the one hour, the SH content was determined to be 0.8 meq/g which strongly suggests that the synthesis of MAN as carried out in Example 1 leads to a considerable amount of the disulfide of MAN which may be reduced to MAN as just described above.

EXAMPLE 3

Example 1 was repeated using the same quantities of reagents but maintaining the reaction under an $H_2S$ atmosphere. The reaction exothermed at a pH of 9.2 and increased the reaction mixture temperature to $-15°$ C. The reaction mixture was worked up in the same fashion as described in Example 1. The resultant product mixture was determined to be 53.3% MAN by iodine titration (mixture SH=7.29 meq/g, theory for 100% MAN=13.67).

EXAMPLE 4

To a 3-neck, 500 ml, round bottomed flask equipped with stirrer, condenser, thermometer and pH probe was added under nitrogen blanket 25.81 g (0.342 moles) ClAN, 25 ml methylene chloride, 0.025 g tetrabutyl ammonium bisulfate and 2 ml distilled water. To this vigorously agitated mixture was added dropwise an aqueous solution containing 19.16 g (0.342 moles) NaSH (NaSH hydrate of 30.6% water content) and 35 ml distilled water. The addition took 51 minutes. The reaction mixture was kept stirring for an additional 94 minutes while keeping the temperature between $-11°$ C. and 4° C. After working up the reaction product in the fashion as desribed in Example 1, it was determined to be 22.0% MAN.

EXAMPLE 5

The reaction of Example 4 was repeated but without adding the tetrabutyl ammonium bilsulfate. The reaction mixture was worked up as also described in Example 1. The reaction product was determined to be 3.0% MAN.

The following example demonstrates the necessity of running the reaction at low temperatures, i.e., −10° C. or below, in order to obtain high MAN yields.

EXAMPLE 6

To a 3-neck, 500 ml, round bottomed flask equipped with stirrer, condenser, thermometer and pH probe was added under $N_2$ blanket 15.32 g (0.273 moles) NaSH (NaSH hydrate of 25.6% water content) and 20 ml of distilled water. 20.64 g (0.273 moles) of ClAN was then added at once while the reaction mixture was submerged into a water/ice bath. The initial pH of the reaction mixture was above 12. During the next 1 minute the pH decreased to 9.0 at which point the mixture exothermed. The temperature increased rapidly to 105° C. After the exotherm a white solid came out of solution (identified as NaCl). Thirty-five minutes after the exotherm occurred (keeping the reaction mixture at or near 20° C.) the reaction mixture was worked up as described in Example 1:

The resultant product was determined to be 1.2% MAN by iodine titration.

The following example demonstrates the criticality of adding the ClAN in mass in order to obtain high MAN yields.

EXAMPLE 7

To a 3-neck, 500 ml, round bottomed flask equipped with stirrer, condenser and thermometer was added under $N_2$ blanket 7.74 g (0.138 moles) NaSH (NaSH hydrate of 35.6 weight % water content) and 7 ml of distilled water. After cooling this mixture to 0° C., 10.32 g (0.137 moles) of ClAN was added dropwise over a period of eight minutes. During the addition, the temperature increased rapidly to 18° C. After the exotherm a white solid came out of solution (identified as NaCl). Ten minutes after the exotherm occurred (keeping the reaction mixture at or near 5° C.), the reaction mixture was worked up in the same fashion as described in Example 1.

The resultant product was determined to be 7.5% MAN by iodine titration (mixture SH=1.03 meq/g, theory for 100% MAN=13.67). The MAN was distilled from this mixture at 34° C. at 2 torr and 39° C. at 5 torr. The analysis of the distilled MAN gave an SH value of 5.0 meq/g (36.6% of theory).

Certainly, reasonable variations and modifications within the scope of this disclosure are possible, yet without departing from the reasonable scope and intended spirit thereof, as shown by the specification itself and by the claims here appended.

We claim:

1. The process of forming mercaptoacetonitrile which comprises reacting in mass a substantially stoichiometric amount of chloroacetonitrile with a 10 to 50 weight % aqueous solution of sodium hydrosulfide at a temperature in the range −25° C. to −10° C. in an inert atmosphere at a pressure ranging from substantially atmospheric up to about 30 mm Hg above atmospheric and maintaining the reaction mixture at a temperature below 5° C. after the exotherm peak.

2. The process according to claim 1 wherein the reaction is carried out in the presence of a liquid medium.

3. The process according to claim 2 wherein the liquid medium is a member of the group consisting of methylene chloride, methyl chloride, ethyl chloride, isopropanol, ethylene glycol and glycerin.

4. The process according to claim 2 wherein 0.05 to 5% by weight of chloroacetonitrile of a salt selected from the group consisting of tricaprylylmethyl ammonium chloride, triethyl benzyl ammonium chloride, hexadecyltributyl phosphonium bromide and tetrabutyl ammonium bisulfate is added to the reaction mixture.

5. The process according to claim 1 characterized in that said reaction of chloroacetonitrile and sodium hydrosulfide is carried out by initially cooling said aqueous sodium hydrosulfide to between −25° C. to −15° C., followed by addition of said chloroacetonitrile and followed subsequently by the maintenance of the reaction mixture, after the exotherm peak and before the workup, at temperatures between −5° C. and +5° C., preferably between −2° C. and +2° C. for 25 to 35 minutes.

6. The process according to claim 5 further characterized in that said workup procedure comprises an acidification step, a vacuum application step to accomplish $H_2S$ removal, a liquid extraction step and a final low pressure vacuum distillation step.

* * * * *